US010806814B2

(12) United States Patent
Kolins et al.

(10) Patent No.: US 10,806,814 B2
(45) Date of Patent: Oct. 20, 2020

(54) STETHOSCOPE AND HAND SANITIZER

(71) Applicants: Mark D. Kolins, Bloomfield Hills, MI (US); Barry Siegel, Birmingham, MI (US)

(72) Inventors: Mark D. Kolins, Bloomfield Hills, MI (US); Barry Siegel, Birmingham, MI (US)

(*) Notice: Subject to any disclaimer, the term of this patent is extended or adjusted under 35 U.S.C. 154(b) by 442 days.

(21) Appl. No.: 15/711,804

(22) Filed: Sep. 21, 2017

(65) Prior Publication Data

US 2018/0008738 A1 Jan. 11, 2018

Related U.S. Application Data

(63) Continuation-in-part of application No. 14/828,651, filed on Aug. 18, 2015, now Pat. No. 9,993,572, which is a continuation of application No. 14/357,523, filed as application No. PCT/US2012/064442 on Nov. 9, 2012, now Pat. No. 9,138,500.

(60) Provisional application No. 62/489,248, filed on Apr. 24, 2017, provisional application No. 62/397,580, filed on Sep. 21, 2016, provisional application No. 61/557,619, filed on Nov. 9, 2011.

(51) Int. Cl.
| | |
|---|---|
| *A61L 2/18* | (2006.01) |
| *A61B 90/70* | (2016.01) |
| *A61L 2/235* | (2006.01) |
| *A61B 7/02* | (2006.01) |
| *A61B 90/80* | (2016.01) |

(52) U.S. Cl.
CPC ............ *A61L 2/18* (2013.01); *A61B 7/02* (2013.01); *A61B 90/70* (2016.02); *A61B 90/80* (2016.02); *A61L 2/235* (2013.01)

(58) Field of Classification Search
CPC . A61L 2/18; A61L 2/235; A61B 90/70; A61B 7/02
See application file for complete search history.

(56) References Cited

U.S. PATENT DOCUMENTS

| | | |
|---|---|---|
| 2005/0214185 A1 | 9/2005 | Castaneda |
| 2009/0238738 A1 | 9/2009 | Hurwitz et al. |
| 2010/0168637 A1* | 7/2010 | Casey ................ A61M 35/003 604/3 |

(Continued)

FOREIGN PATENT DOCUMENTS

WO WO-2010131253 A2 11/2010

OTHER PUBLICATIONS

PCT International Search Report for PCT/US2012/064442, dated Jan. 25, 2013.
Office Action for U.S. Appl. No. 14/357,523 dated Jan. 29, 2015.

*Primary Examiner* — Sean E Conley
(74) *Attorney, Agent, or Firm* — Honigman LLP

(57) ABSTRACT

An apparatus for sanitizing is provided. The apparatus includes a housing having a reservoir for retaining sanitizing fluid. The apparatus also includes a holder disposed beneath the housing. The apparatus further includes an applicator pad received by the holder and adapted to be in selective fluid communication with the reservoir. The applicator pad includes a dome-shaped portion having a substantially hemispherical shape configured to extend into an interior region of a bell of a stethoscope head when the bell is placed over the dome-shaped portion.

22 Claims, 8 Drawing Sheets

(56) References Cited

U.S. PATENT DOCUMENTS

2012/0273003 A1* 11/2012 Holloway ................ A61L 2/16
134/6

* cited by examiner

STETHOSCOPE AND HAND SANITIZER

CROSS REFERENCE TO RELATED APPLICATIONS

This U.S. patent application claims priority under 35 U.S.C. § 119(e) to U.S. Provisional Application 62/397,580, filed on Sep. 21, 2016 and U.S. Provisional Application 62/489,248, filed on Apr. 24, 2017. The disclosures of these prior applications are considered part of the disclosure of this application and are hereby incorporated by reference in their entireties. Furthermore, this U.S. patent application is a continuation-in-part of pending U.S. patent application Ser. No. 14/828,651 (Publication No. 20150352237) and incorporates by reference, in their entireties, commonly owned U.S. Pat. No. 9,138,500 and U.S. patent application Ser. No. 14/828,651 (Publication No. 20150352237).

TECHNICAL FIELD

This disclosure relates to a medical equipment sanitizer and more particularly to an apparatus for sanitizing hands and stethoscopes.

BACKGROUND

Hospital-acquired infections are an issue in today's healthcare system. Such infections can lengthen hospital stays and increase health care costs. Hospital-acquired infections have many causes, including the transmission pathogenic microorganisms by contaminated medical devices. For this reason, the American Medical Association has passed a resolution recommending that stethoscopes (and other handheld medical instruments) be cleaned between uses. See American Medical Association House of Delegates. *Proceedings of the 50th Interim Meeting.* Chicago, Ill.: American Medical Association; December 8-11, 1996:398. A need remains for a fast, easy, and cost-effective way to clean and to disinfect stethoscope heads between patient uses.

SUMMARY

One aspect of the disclosure provides an apparatus for sanitizing. The apparatus includes a housing having a reservoir for retaining sanitizing fluid and a holder disposed beneath the housing. The apparatus also includes an applicator pad received by the holder and adapted to be in selective fluid communication with the reservoir. The applicator pad includes a dome-shaped portion having a substantially hemi-spherical shape configured to extend into an interior region of a bell of a stethoscope head when the bell is placed over the dome-shaped portion.

Implementations of the disclosure may include one or more of the following optional features. In some implementations, the apparatus includes a dispensing valve for dispensing the sanitizing fluid, the dispensing valve facing the applicator pad. The dispensing valve may have a dispensing state and a non-dispensing state. The dispensing valve may be configured to dispense the sanitizing fluid from the dispensing valve on the applicator pad only when the dispensing valve is in the dispensing state. The lever may be configured to activate the dispensing valve to transition from the non-dispensing state to the dispensing state. Optionally, the applicator pad and the dispensing valve may be offset by a dispensing distance. The dispensing distance may be defined by a dispersion area of the sanitizing fluid from the dispensing valve. The dispersion area may have a dimensional proportionality to a wetting area of the applicator pad.

In some examples, the applicator pad is an absorbent material to absorb the sanitizing fluid. In this example, the absorbent material of the applicator pad may be porous and may include at least one of a cloth material, a cellulose sponge material, or a synthetic polymer sponge material. Additionally or alternatively, the applicator pad may further include a substantially planar portion configured to receive a diaphragm of the stethoscope head when a surface of the diaphragm is placed in contact with the substantially planar portion of the applicator pad. Optionally, the substantially hemi-spherical shape of the dome-shaped portion may have a radius between about 0.50 cm and 1.00 cm.

In some configurations, when the apparatus includes a lever configured to activate the dispensing valve to transition from the non-dispensing state to the dispensing state, the apparatus also includes a passage from the reservoir to the applicator pad. Here, the activation of the lever may dispense sanitizing fluid through both the dispensing valve and the passage to the applicator pad. Additionally or alternatively, the passage may be configured for fluid communication with the applicator pad independently from the dispensing valve. Here, the apparatus may include more than one lever, the more than one lever may include a passage lever configured to dispense sanitizing fluid through the passage and a dispensing valve lever. In some implementations, the apparatus further includes a mount disposed on the housing, the mount configured for wall-mounting and having one or more slots on the housing. The one or more slots may be configured to receive a fastener for mounting the housing.

Another aspect of the disclosure provides an apparatus for sanitizing. The apparatus includes a housing having a reservoir for retaining sanitizing fluid. The apparatus also includes a holder disposed beneath the housing. The holder includes a dome-shaped portion having a substantially hemi-spherical shape configured to extend into an interior region of a bell of a stethoscope head when the bell is placed over the dome-shaped portion. The apparatus further includes an applicator pad received by the holder and adapted to be in selective fluid communication with the reservoir. The apparatus also includes a dispensing valve coupled to the housing and facing the applicator pad. The dispensing valve is configured to dispense the sanitizing fluid.

This aspect may include one or more of the following optional features. In some configurations, the applicator pad has a top surface and an opposite bottom surface. The top surface may face the dispensing valve and the bottom surface may have a concave region for receiving the dome-shaped portion of the holder. The top surface of the applicator pad may be substantially planar. The apparatus may further include a lever. The lever may be configured to activate the dispensing valve to transition from a non-dispensing state to a dispensing state. Additionally or alternatively, the applicator pad and the dispensing valve may be offset by a dispensing distance. The dispensing distance may be defined by a dispersion area of the sanitizing fluid from the dispensing valve. The dispersion area may further have a dimensional proportionality to a wetting area of the applicator pad.

Another aspect of the disclosure provides an apparatus for sanitizing. The apparatus includes a housing having a front wall and a back wall. The housing encases a reservoir for retaining sanitizing fluid. The apparatus also includes an applicator pad mounted on the front wall of the housing and adapted to be in selective fluid communication with the reservoir. The applicator pad includes a dome-shaped portion having a substantially hemi-spherical shape configured to extend into an interior region of a bell of a stethoscope head when the bell is placed over the dome-shaped portion. The apparatus further includes a dispensing valve coupled to the housing adjacent to the applicator pad on the front wall of the housing. The dispensing valve has a non-dispensing state and a dispensing state. The dispensing valve is configured to dispense the sanitizing fluid when in the dispensing state. The apparatus also includes a mount disposed on the back wall of the housing. The mount is configured for wall-mounting and has one or more slots in the back wall of the housing. The one or more slots is configured to receive a fastener for mounting the housing The details of one or more implementations of the disclosure are set forth in the accompanying drawings and the description below. Other aspects, features, and advantages will be apparent from the description and drawings, and from the claims.

DESCRIPTION OF DRAWINGS

FIG. 1B is a front perspective view of an apparatus for dispensing sanitizing fluid.

Like reference symbols in the various drawings indicate like elements.

DETAILED DESCRIPTION

Today, the healthcare industry is a fast-paced environment where healthcare workers strive to maintain sterility to prevent the transfer of pathogenic microorganisms from patient to patient or from patient to healthcare worker. Due to the fast pace of the healthcare environment, healthcare workers need cost-effective and efficient solutions to minimize the time required to sterilize their hands and their healthcare equipment. One aspect of the disclosed sanitizing apparatus is that healthcare workers may sterilize their hands and their stethoscopes at a single system. Some advantages to a single system are that a healthcare worker may reduce changeover time between patients and/or a healthcare worker may be reminded by the physical apparatus to sanitize both his/her hands and stethoscope. In other words, the sanitizing apparatus may enable a healthcare worker to have a turnkey sanitizing system. Therefore, utilizing the principles disclosed herein, healthcare workers are able to quickly, easily, and cost-effectively sanitize both their stethoscope heads and their hands between patient uses at the point of care.

Figure 1A:
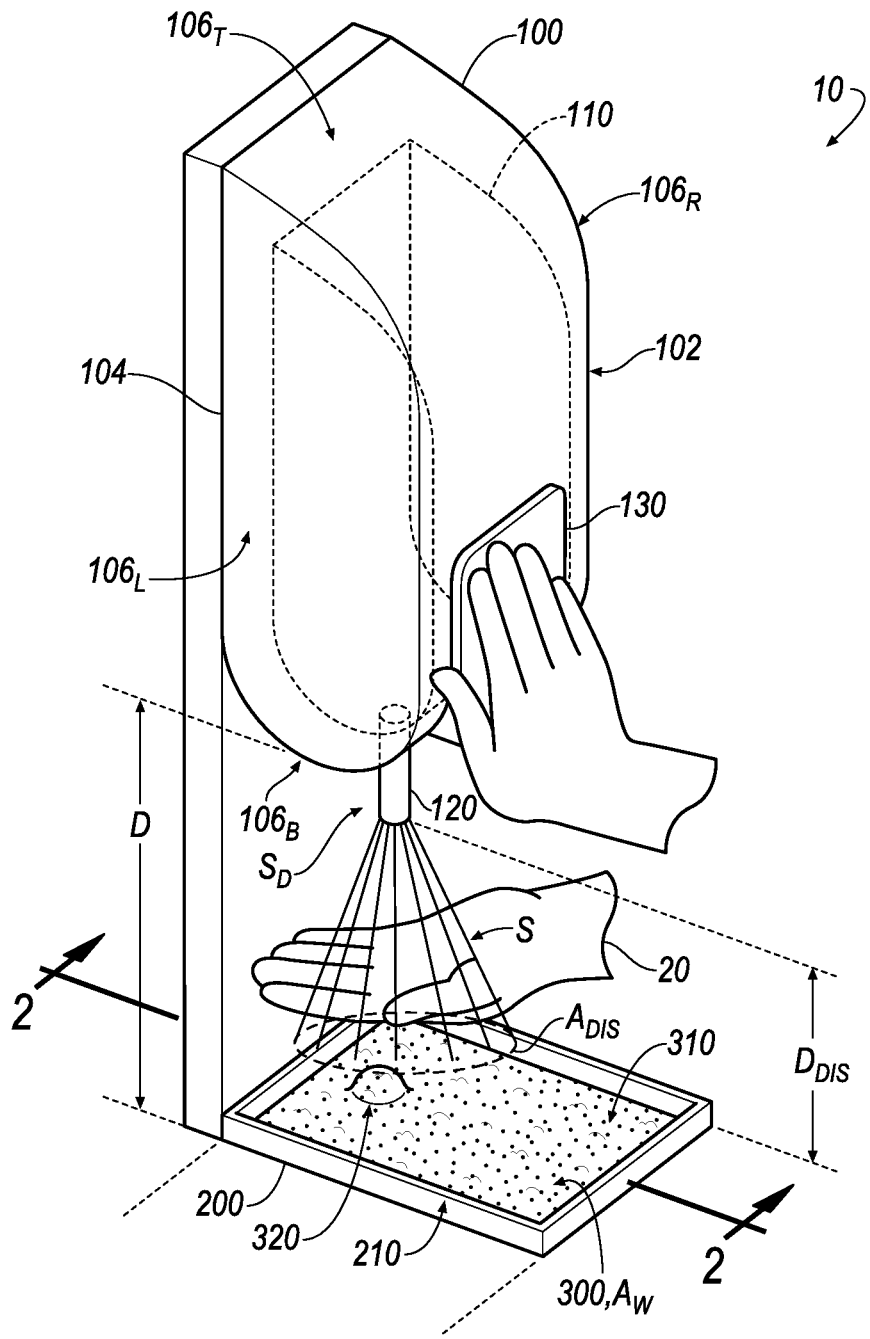
FIGS. 1A-1C are front perspective views of an apparatus for dispensing sanitizing fluid.
Figure 1B:
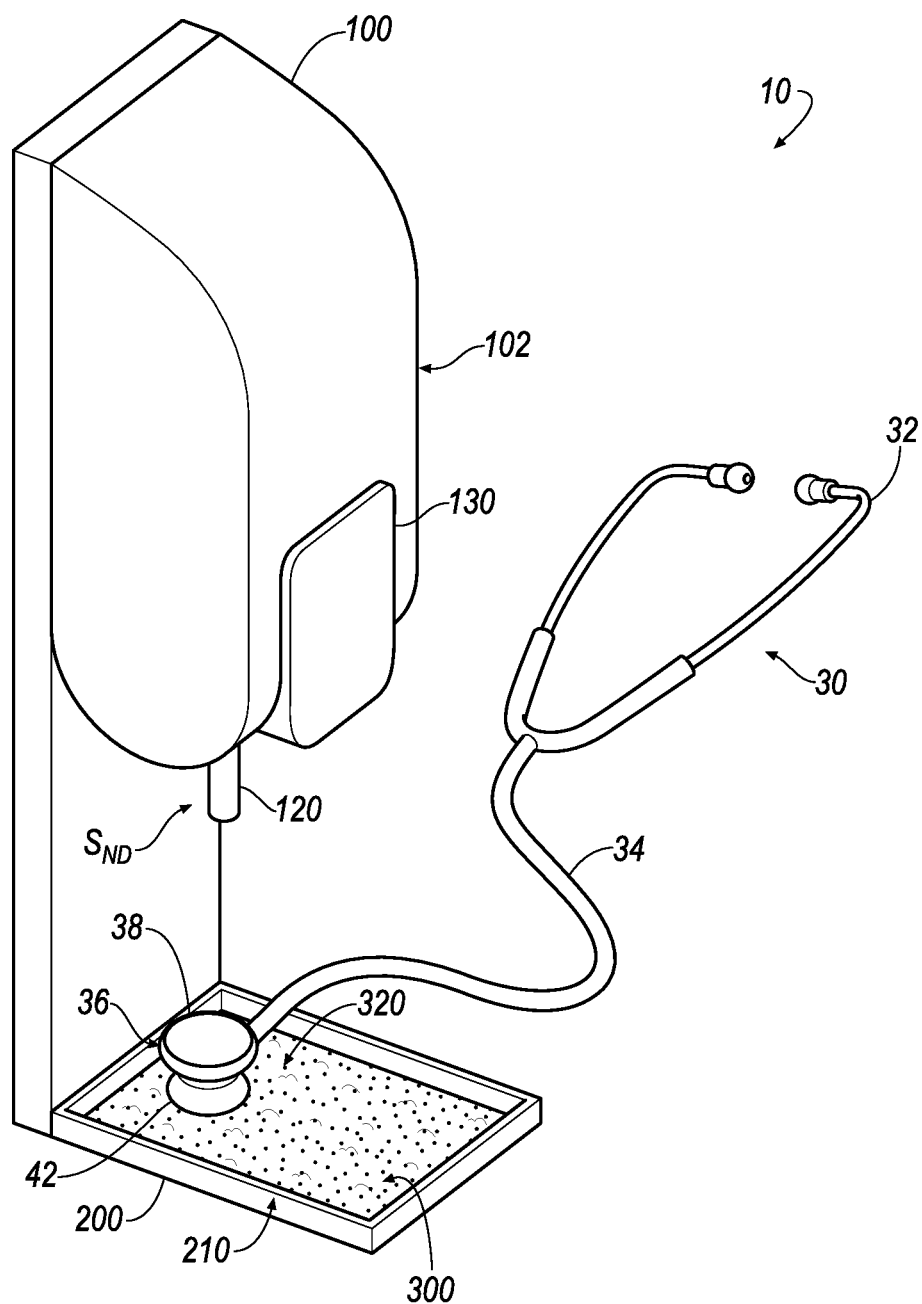
Figure 1C:
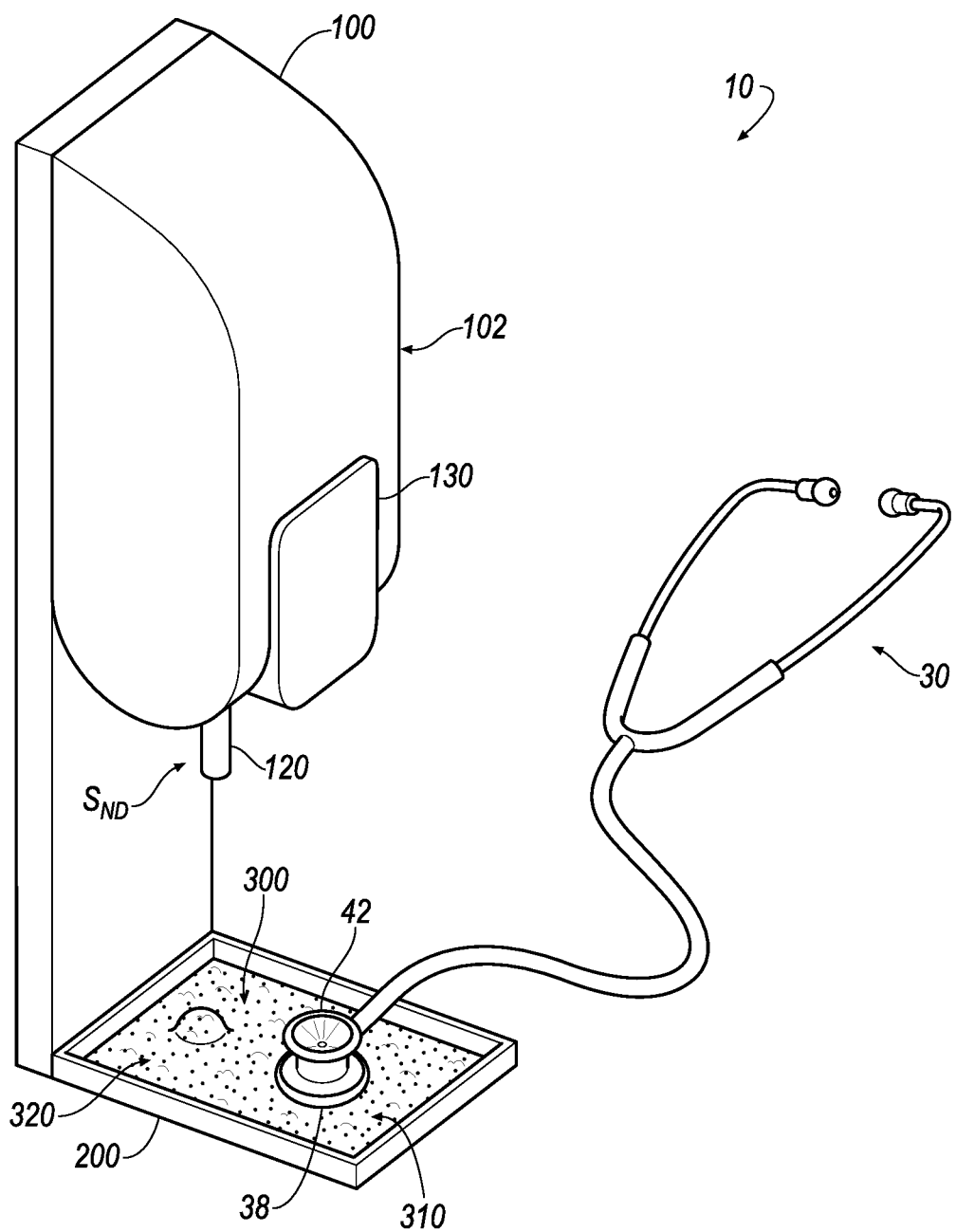

FIGS. 1A-1C illustrate front perspective views of an apparatus 10 for dispensing sanitizing fluid S. FIG. 1A depicts the apparatus 10 dispensing sanitizing fluid S for hands of a user 20. While, FIGS. 1B and 1C depict the apparatus 10 dispensing sanitizing fluid S onto at least one applicator pad 300 to sanitize a stethoscope 30.

The apparatus 10 generally includes a housing 100, a holder 200, and one or more applicator pads 300. The housing 100, as illustrated in FIGS. 1A-1C, has a rounded rectangular shape. In this embodiment, the housing 100 has a front wall 102, a back wall 104, and side walls 106, including a top wall $106_T$, a bottom wall $106_B$, a left wall $106_L$, and a right wall $106_R$. However, as one having ordinary skill in the art will readily understand, the housing 100 may have any suitable shape.

The housing 100 further includes a reservoir 110. FIG. 1A illustrates the reservoir 110 by a dotted line internal to the housing 100. Although FIG. 1A includes the dotted line, it may be presumed that any apparatus 10 disclosed herein has a reservoir 110. The reservoir 110 is disposed within the housing 100 and is configured to retain the sanitizing fluid S. For example, in FIG. 3B, the upper left corner of the housing 100 is cut away to reveal the reservoir 110 inside the housing 100. In some embodiments (not shown), the walls of the housing 100 itself define the reservoir 110. In these embodiments, the supply of sanitizing fluid S may be replenished by pouring additional sanitizing fluid into the housing 100 through an aperture (not shown). In other embodiments, the reservoir 110 is a separate container inside the housing 100. For example, as shown in FIG. 1A (by the dotted line), the reservoir 110 may be a bag within which the sanitizing fluid S is contained. In these embodiments, the supply of sanitizing fluid S may be replenished by replacing an empty bag with a new bag full of sanitizing fluid S.

The holder 200 is disposed beneath the housing 100. For example, FIGS. 1A-1C depict the holder 200 facing the bottom wall 106E of the housing 100. The holder 200 is positioned at a distance D away from the housing 100 such that the distance D enables a user 20 to position his or her hands between the housing 100 and the holder 200. The holder 200 may be mounted to secure the holder 200 at the distance D from the housing 100. In some examples, the holder 200 is mounted to a frame that may additionally be part of the apparatus 10. In other examples, the holder 200 is mounted to a wall or other member perpendicular to the holder 200 to maintain the distance D. In yet other implementations, the holder 200 is coupled to the housing 100. For example, the holder 200 may be secured in position because the holder 200 is mounted to the back wall 104 of the housing 100. In these examples, the back wall 104 extends past the bottom wall 106E of the housing 100 at least the distance D to secure the holder 200 in place. The holder 200 is configured to retain the one or more applicator pads 300. In some examples, the holder 200 includes a perimeter wall 210. The perimeter wall 210 may surround the at least one applicator pad 300 such that the applicator pad 300 remains in place as the stethoscope 30 applies pressure and/or friction to the at least one applicator pad 300 during sanitization.

The one or more applicator pads 300 is configured to apply the sanitizing fluid S to the stethoscope 30. In some examples, one or more applicator pads 300 are adapted to be in selective fluid communication with the reservoir 110. In some implementations, the at least one applicator pad 300 is received by the holder 200. For example, the at least one applicator 300 is seated within the perimeter wall 210 of the holder 200. In other examples, the holder 200 is a sleeve or a channel into which the at least one applicator pad 300 is inserted. Additionally or alternatively, the at least one applicator pad 300 may be mounted on any wall or walls of the housing 100. For example, FIG. 3B particularly illustrates that the applicator pad 300 is mounted to the front wall 102 of the housing 100.

In some embodiments, the applicator pad 300 is constructed from a porous, absorbent material configured to absorb the sanitizing fluid S. For example, the applicator pad 300 may be constructed from a cloth material, a cellulose sponge material, a synthetic polymer sponge material, or any other suitably porous and absorbent material. In some embodiments, the applicator pad 300 has a thickness 300t sufficient to absorb an effective quantity of sanitizing fluid S to sanitize a stethoscope 30. The effective quantity of sanitizing fluid S may differ depending on the particular sanitizing fluid S used with a given apparatus 10.

Referring to FIGS. 1B and 1C, generally, the stethoscope 30 has a structure that includes a headset 32 connected by a tube 34 to a chest piece 36. The chest piece 36 often includes a diaphragm 38 and a bell 42 connected to the tube 34 at a stem 44 (shown in FIGS. 1B and 1C). Typically, the chest piece 36 generates different acoustics to the headset 32 depending on whether the user 20 uses the diaphragm 38 or the bell 42. The diaphragm 38 with a flat surface is capable of transmitting higher frequency sounds than the bell 42; while the bell 42 has a hemi-spherical shape acoustically configured to transmit lower frequency sounds than the diaphragm 38. The apparatus 10 is configured to sanitize at least one of the diaphragm 38 and/or the bell 42.

Figure 2A:
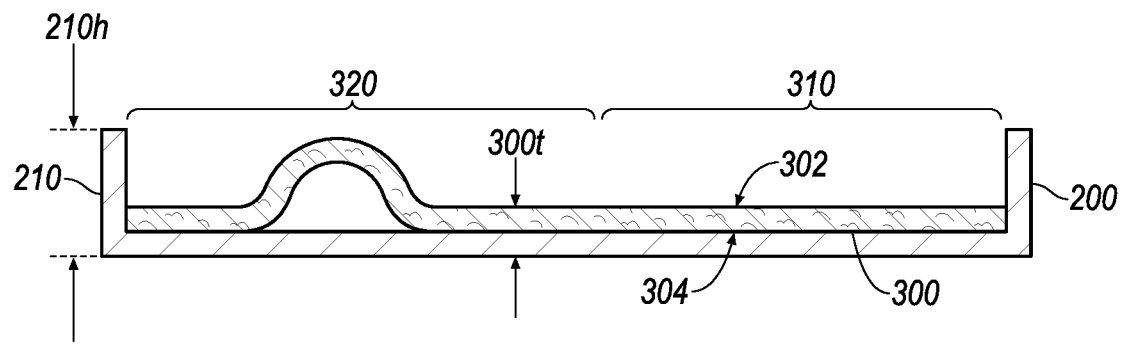
FIGS. 2A and 2B are cross sectional views of portions of an apparatus for dispensing sanitizing fluid along line 2-2 of FIG. 1A.
Figure 2B:
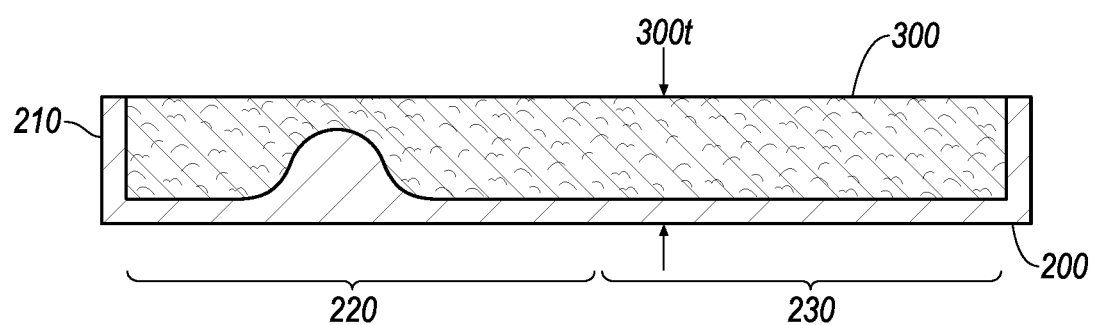

The applicator pad 300 includes a top surface 302 and an opposite bottom surface 304 (shown in FIGS. 2A and 2B). In some embodiments, the applicator pad 300 is configured to facilitate the application of sanitizing fluid S to the diaphragm 38 and/or the bell 42 of the stethoscope 30. Thus, the applicator pad 300 may have a substantially planar portion 310, shown in FIGS. 1A-2B, for applying the sanitizing fluid S to the flat surface of the diaphragm 38 of the stethoscope 30. The applicator pad 300 also may have a raised portion for example such as a dome-shaped portion 320 for applying the sanitizing fluid S to the inside of the bell 42 of the stethoscope 30. The raised portion is configured in a shape suitable to extend at least partially into the bell 42 of the stethoscope 30. For example, the raised portion may have a substantially hemi-spherical shape 320, with a radius between about 0.50 and about 1.00 cm, permitting the dome-shaped portion 320 to extend at least partially into the bell 42. In other embodiments, the applicator pad 300 is configured to accommodate alternately shaped stethoscope chest pieces 36 or other devices. A conical, or frustoconical shaped raised portion may also work well depending on the geometry of the bell 42 of the stethoscope 30.

The substantially planar portion 310 and the dome-shaped portion 320 of the applicator pad 300 may be disposed adjacent to one another within the holder 200 or on the housing 100. As some examples, FIGS. 2A and 2B depict the substantially planar portion 310 and the dome-shaped portion 320 of the applicator pad 300 disposed adjacent to one another within the holder 200; whereas, FIG. 3B depicts the substantially planar portion 310 and the dome-shaped portion 320 adjacent to each other on the housing 100. In some embodiments, the substantially planar portion 310 and the dome-shaped portion 320 are formed from a single piece of porous, absorbent material, defining a single applicator pad 300. In other embodiments, the substantially planar portion 310 and the dome-shaped portion 320 may be formed from separate pieces of porous, absorbent material, defining more than one applicator pads 300, and/or may be disposed on non-adjacent portions of the housing 100 and/or the holder 200.

The housing 100 may further include a dispensing valve 120 for dispensing the sanitizing fluid S from the reservoir 110 onto the applicator pad 300. The dispensing valve 120 faces the applicator pad 300 such that the outlet of the dispensing valve 120 dispenses the sanitizing fluid S toward the top surface 302 of the applicator pad 300. In one embodiment, the dispensing valve 120 has a dispensing state SD and a non-dispensing state SND, and is configured to dispense the sanitizing fluid S from the reservoir 110 onto the applicator pad 300 only when the dispensing valve 120 is in the dispensing state SD.

In some implementations, the dispensing valve 120 is configured to dispense the sanitizing fluid S from the reservoir 110 onto the applicator pad 300 when a lever 130, disposed on the housing 100, activates the dispensing valve 120. For example, the lever 130 may be activated by pressure (e.g., pushed by a hand of the user 20 as shown in FIG. 1A) or by sensor, such as a proximity sensor (not shown). Generally, the lever 130 may refer to any mechanical or electrical switch that activates the dispensing valve 120 such that when the lever 130 activates the dispensing valve 120, the dispensing valve 120 is configured to deliver an aliquot of sanitizing fluid S to the user 20 and/or to the applicator pad 300. In some configurations, the lever 130 may function as a pump to, in conjunction with a dispensing means (e.g., dispensing valve 120 or passage 140), dispense the sanitizing fluid S. In one embodiment, the dispensing valve 120 is configured to deliver a sufficiently large aliquot of sanitizing fluid S to saturate the applicator pad 300 and/or user 20 with the sanitizing fluid S. One advantage of the apparatus 10 is that when the dispensing valve 120 dispenses the sanitizing fluid S onto the user 20 (e.g., the hands of the user 20), excess sanitizing fluid S may be caught and retained by the applicator pad 300. Therefore, the apparatus 10 may reduce an amount of wasted sanitizing fluid S. By capturing access sanitizing fluid S, some configurations of the apparatus 10 may allow healthcare providers to reduce the cost of sanitizing fluid S. Additionally or alternatively, the lever 130 may be activated prior to or subsequent to dispensing sanitizing fluid S to the user 20 in order to saturate the at least one applicator pad 300 with sanitizing fluid S for the stethoscope 30.

Although, the dispensing valve 120 for dispensing the sanitizing fluid S from the reservoir 110 is commonly illustrated as a cylindrical component throughout the figures. It will be understood that the dispensing valve 120 may be any suitable valve known in the art for controllably delivering aliquots of a fluid. Moreover, it will be understood that a nozzle may be used in conjunction with the dispensing valve 120 to direct the sanitizing fluid S onto the at least one applicator pad 300. For example, the dispensing valve 120 may be a mechanical pump, such as a pump that discharges the sanitizing fluid S upon the depression of a plunger, or an electric pump powered by direct or alternating current. Additionally or alternatively, the dispensing valve 120 may also be a plurality of orifices or valves in a deflectable wall portion (e.g., the bottom wall $106_B$) of the housing 100.

Referring to FIG. 1A, a user 20 presses the lever 130 to activate the dispensing valve 120. FIG. 1A depicts the lever 130 integrated into the front wall 102 of the housing 100 such that the lever 130 depresses into the housing 100 to activate the dispensing valve 120. When the dispensing valve 120 is activated by the lever 130, the dispensing valve 120 transitions from the non-dispensing state SND (not shown) to the dispensing state SD. As depicted in FIG. 1A, the user 20 has his or her hands between the holder 200 and the housing 100 such that the hands of the user 20 receive the sanitizing fluid S dispensed by activation of the dispensing valve 120 from the reservoir 110. FIG. 1A also illustrates that the sanitizing fluid S may disperse through the hands of the user 20 and/or around the hands of the user 20 such that the applicator pad 300 also receives sanitizing fluid S during user sanitizing. The cross-hatched applicator pad 300 indicates the applicator pad 300 receives sanitizing fluid S.

Referring to FIG. 1B, the bell 42 of the stethoscope 30 is positioned on the dome-shaped portion 320 of the applicator pad 300. With the bell 42 of the stethoscope 30 positioned on the dome-shaped portion 320 of the applicator pad 300, the sanitizing fluid S within the applicator pad 300 transfers to the bell 42 of the stethoscope 30 to provide sanitization. When in this position, the hemi-spherical shape of the dome shaped portion 320 extends into an interior region of the bell 42 and contacts a surface of the bell 42 in the interior region. In some examples, the position of the bell 42 on the dome-shaped portion 320 occurs after the sanitizing of the hands of the user 20 (shown in FIG. 1A). In other examples, FIG. 1B occurs independently of the sanitizing of the hands of the user 20. In these examples, the user 20 may activate the dispensing valve 120 merely to saturate the applicator pad 300 and to sanitize the bell 42 of the stethoscope 30.

Referring to FIG. 1C, the diaphragm 38 of the stethoscope 30 is positioned on the substantially planar portion 310 of the applicator pad 300. With the diaphragm 38 of the stethoscope 30 positioned on the substantially planar portion 310 of the applicator pad 300, the sanitizing fluid S within the applicator pad 300 transfers to the diaphragm 38 of the stethoscope 30 to provide sanitization. In some examples, the position of the diaphragm 38 on the substantially planar portion 310 occurs after the sanitizing of the hands of the user 20 (shown in FIG. 1A). In other examples, FIG. 1C occurs independently of the sanitizing of the hands of the user 20. In these examples, the user 20 may activate the dispensing valve 120 merely to saturate the applicator pad 300 and to sanitize the diaphragm 38 of the stethoscope 30.

In some examples, such as FIGS. 1A-1C, the applicator pad 300 and the dispensing valve 120 are offset by a dispensing distance $D_{dis}$. In some embodiments, the dispensing distance $D_{dis}$ may be substantially equal to the distance D the holder 200 is positioned away from the housing 100. The apparatus 10 may be configured such that the dispensing distance $D_{dis}$ generates a dispersion area $A_{dis}$ of the sanitizing fluid S from the dispensing valve 120. In some implementations, at the dispensing distance $D_{dis}$, the dispersion area $A_{dis}$ has an area that is substantially equal to or less than a wetting area 330 of the applicator pad 300. The wetting area 330 of the applicator pad 300 is generally equal to the area of one of the substantially planar portion 310 or the dome-shaped portion 320, or both the substantially planar portion 310 and the dome-shaped portion 320. Thus, in these implementations, the wetting area 330 and the dispersion area $A_{dis}$, at the dispensing distance Dais, have dimensional proportionality. In some examples, the at least one applicator pad 300 is circular to correspond to a circular shape of the dispersion area $A_{dis}$. In these examples, the holder 200 may also be circular to accommodate for the applicator pad 300.

Referring to FIGS. 2A and 2B, in some examples, the structure of the holder 200 and/or the applicator pad 300 varies depending on the type of sanitizing fluid S and/or design preferences. In some embodiments, such as FIG. 2A, the applicator pad 300 includes the dome shaped portion 320 with a substantially hemi-spherical shape to extend into the interior region of the bell 42 of the stethoscope 30. As mentioned above, the dome shaped portion 320 may be coupled with or separate from a substantially planar portion 310 of the applicator pad 300. For example, FIG. 2A depicts the applicator pad 300 being a unitary construction with the dome-shaped portion 320 adjacent to the substantially planar portion 310. In some configurations, the at least one applicator pad 300 may be contained within the perimeter wall 210 of the holder 200 such that the perimeter wall 210 has a height 210h that is greater than (FIG. 2A) or equal to (FIG. 2B) the thickness t of the at least one applicator pad 300.

In FIGS. 2A and 2B, the bottom surface 304 of the applicator pad 300 is disposed on the holder 200. For example, the bottom surface 304 of the applicator pad 300 faces away from the dispensing valve 120. In some embodiments, portions of the bottom surface 304 of the applicator pad 300 do not contact the holder 200. For example, within the dome-shaped portion 320, the applicator pad 300 may be raised to form the semi hemi-spherical shape of the dome-shaped portion 320. In other words, the top surface 302 may have a convex region protruding from the holder 200. In other examples, the dome-shaped portion 320 of the applicator pad 300 is formed such that the bottom surface 304 of the applicator pad 300 maintains contact with the holder 200. Additionally or alternatively, within the dome-shaped region 320, the applicator pad 300 may extend further than the perimeter wall 210 of the holder 200.

FIG. 2B is an example where the holder 200 includes a dome shaped portion 220. For example, the dome-shaped portion 220 is formed within the holder 200. In some examples, during sterilization of the bell 42 of the stethoscope 30, the applicator pad 300 compresses in a region above the dome shaped portion 220 of the holder 200 to permit a substantially hemispherical shape of dome-shaped portion 220 of the holder 200 to extend into the interior region of the bell 42. In other words, the user 20 may place the bell 42 over the dome-shaped portion 220 of the holder 200 and compresses the applicator pad 300 into the interior region of the bell 42. In some embodiments, when the holder 200 has the dome-shaped portion 220, the bottom surface 304 of the at least one applicator pad 300 has a concave region for receiving the dome-shaped portion 220 of the holder 200. One advantage of the holder 200 having the dome-shaped portion 220 rather than the applicator pad 300 having the dome shaped portion 320 is that the top surface 302 of the applicant pad 300 may be substantially planar. This may be an advantage because the applicator pad 300 may reduce the wetting area 330, the size of the applicator pad 300, and/or the consumption of sanitizing fluid S. With a reduced wetting area 330, the at least one applicator pad 300 may saturate with less sanitizing fluid S. Another potential advantage is that the at least one applicator pad 300 may conceal the dome shaped portion 220 because, to the user 20, it may look like a flat top surface. When the holder 200 includes the dome shaped region 220, the holder 200 may or may not also include a substantially planar portion 230. For example, although FIG. 2B depicts the holder 200 having the substantially planar portion 230, the top surface 302 of the at least one applicator pad 300 may already include a substantially planar portion 310 to sanitize the diaphragm 38 of the stethoscope 30 such that an additional planar portion in the holder 200 may be a design preference.

Figure 3A:
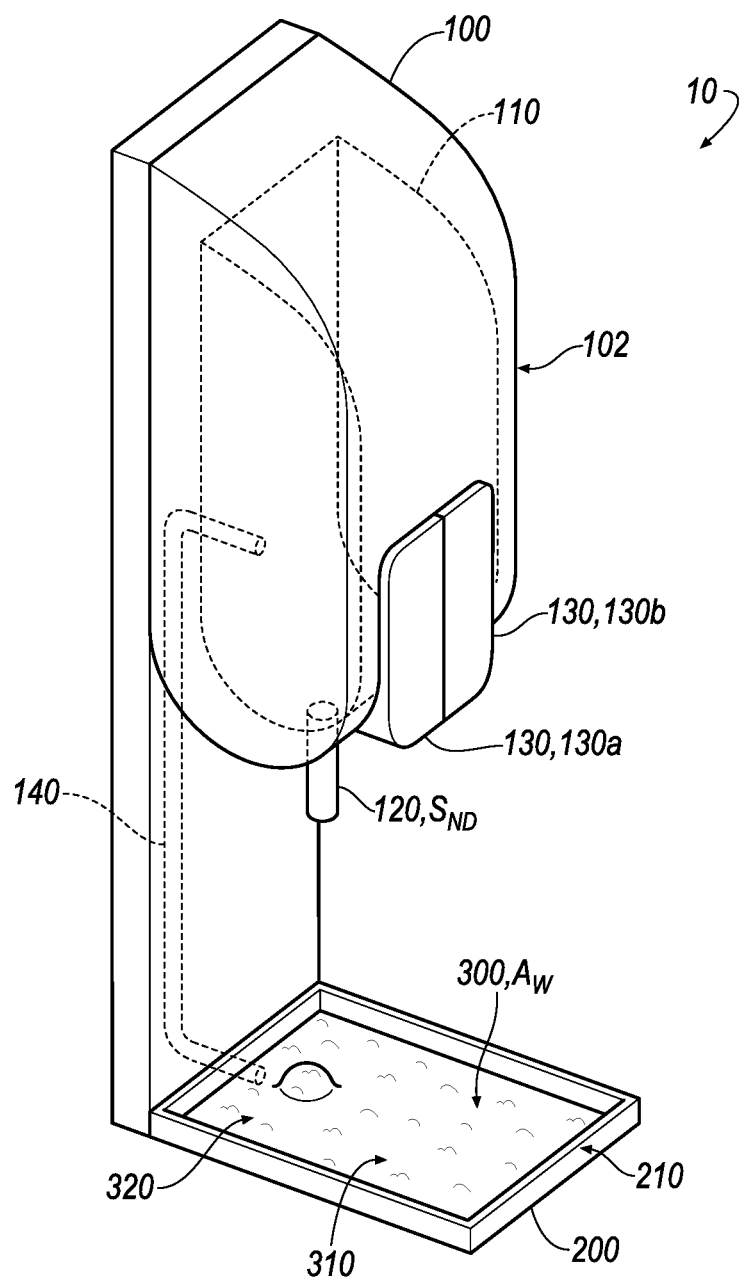
FIGS. 3A and 3B are front perspective views of an apparatus for dispensing sanitizing fluid.
Figure 3B:
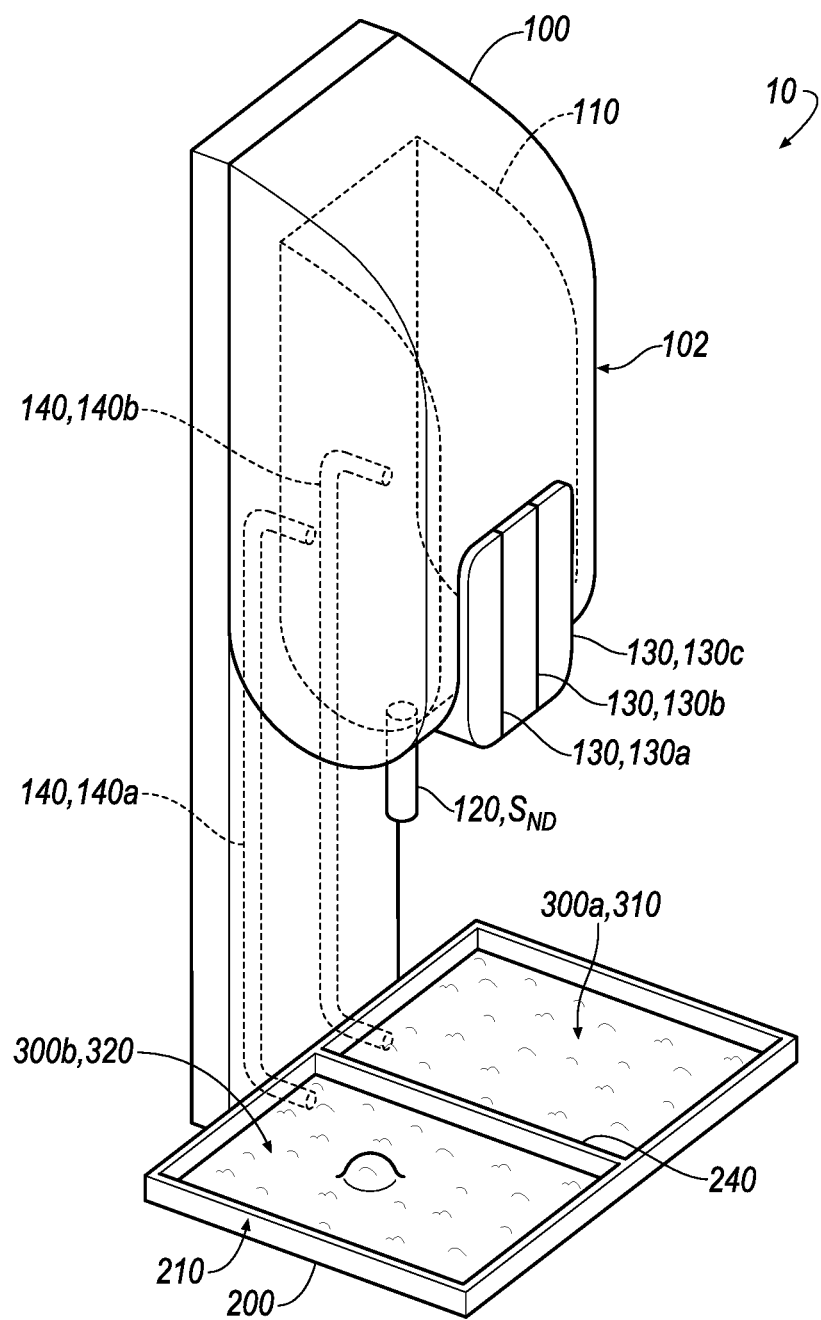

FIGS. 3A and 3B are examples that the apparatus 10 may also include at least one passage 140 and/or more than one lever 130. The at least one passage 140 is configured to fluidly communicate between the reservoir 110 and the at least one applicator pad 300. In some examples, the passage 140 includes a valve for dispensing the sanitizing fluid S from the reservoir 110 when the valve is activated for dispensing. This valve for dispensing may be similar to the dispensing valve 120 such that the valve may be any suitable valve known in the art for controllably delivering aliquots of a fluid. The at least one passage 140 may be partially or wholly disposed within the housing 100. For example, the at least one passage 140 has a dispensing inlet into a portion of the reservoir 110 and a dispensing outlet at the holder 200. In some examples, the passage 140 is directed through a wall or frame upon which the housing 100 is mounted. In some implementations, the holder 200 includes an aperture to receive the dispensing outlet of the at least one passage 140 to transfer the sanitizing fluid S to the at least one applicator pad 300.

In some examples, a single lever 130 or actuator activates to dispense sanitizing fluid S through both the dispensing valve 120 and the at least one passage 140. In other examples, the dispensing valve 120 and the at least one passage 140 may be configured to dispense sanitizing fluid S independently. For example, the passage 140 may be in a non-dispensing state SND when the dispensing valve 120 is in the dispensing state SDIS or vice versa. FIG. 3A is an illustration where the apparatus 10 includes two levers 130, 130a-b to independently operate the passage 140 and the dispensing valve 120. In this example, when the first lever 130, 130a is activated, sanitizing fluid S is dispensed from the reservoir 110 through the dispensing valve 120. Similarly, when the second lever 130, 130b is activated, sanitizing fluid S is dispensed from the reservoir 110 through the passage 140. In some configurations, the more than one lever 130 may be a combination of mechanical/electrical switches and/or mechanical/electrical pumps capable of actuating the passage 140 and/or the dispensing valve 120 to dispense sanitizing fluid S. Moreover, in yet other examples, the dispensing valve 120 and the at least one passage 140 may be configured to independently dispense different types of sanitizing fluid S such that the apparatus 10 may include more than one reservoir 110 for each type of sanitizing fluid S.

FIG. 3B illustrates an apparatus 10 that includes more than one applicator pads 300, 300a-b. In some examples, the holder 200 includes a divider wall 240 to retain the more than one applicator pad 300. The divider wall 240 may be in addition to or an alternative of the perimeter wall 210. In some implementations where the apparatus 10 includes more than one applicator pad 300, the apparatus 10 separately includes a substantially planar applicator pad 300a, 310 and a dome shaped applicator pad 300b, 320. Additionally or alternatively, the apparatus 10 includes more than one passage 140 to communicate sanitizing fluid S to each applicator pad 300. For example, as depicted in FIG. 3B, the first passage 140, 140a connects the reservoir 110 to the dome shaped applicator pad 300b, 320 and the second passage 140, 140b connects the reservoir 110 with the substantially planar applicator pad 300a, 310. Although two passages are shown, any number of passages 140 may be in fluid communication with more than one applicator pads 300. For example, one applicator pad 300 has a receives sanitizing fluid S from a passage 140; while, another applicator pad 300 receives sanitizing fluid S from the dispensing valve 120. In some configurations with more than one applicator pad 300, the applicator pads 300 may be aligned such that the dispensing valve 120 dispenses sanitizing fluid S to each applicator pad 300 regardless of whether a passage 140 is associated with an applicator pad 300.

Referring further to concepts embodied by FIG. 3A, the housing 100 may further include a lever 130 for each means of fluid communication for the sanitizing fluid S to the at least one applicator pad 300. As an example, FIG. 3A depicts three levers 130, 130a-c configured to communicate the sanitizing fluid S to the substantially planar applicator pad 300a, 310 and the dome shaped applicator pad 300b, 320. In this example, a first lever 130, 130a controls the dispensing valve 120; a second lever 130, 130b controls the first passage 140, 140a; and a third lever 130, 130c controls the second passage 140, 140b. By "controls," it is meant that each lever is configured to activate a supply of sanitizing fluid S. Here, with a lever 130 for each dispensing means (e.g., the first passage 140a, the second passage 140b, and the dispensing valve 120), the user 20 may selectively dispense sanitizing fluid S depending on a desired operation (e.g., sanitizing hands, sanitizing the bell 42, and/or sanitizing the diaphragm).

Figure 4:
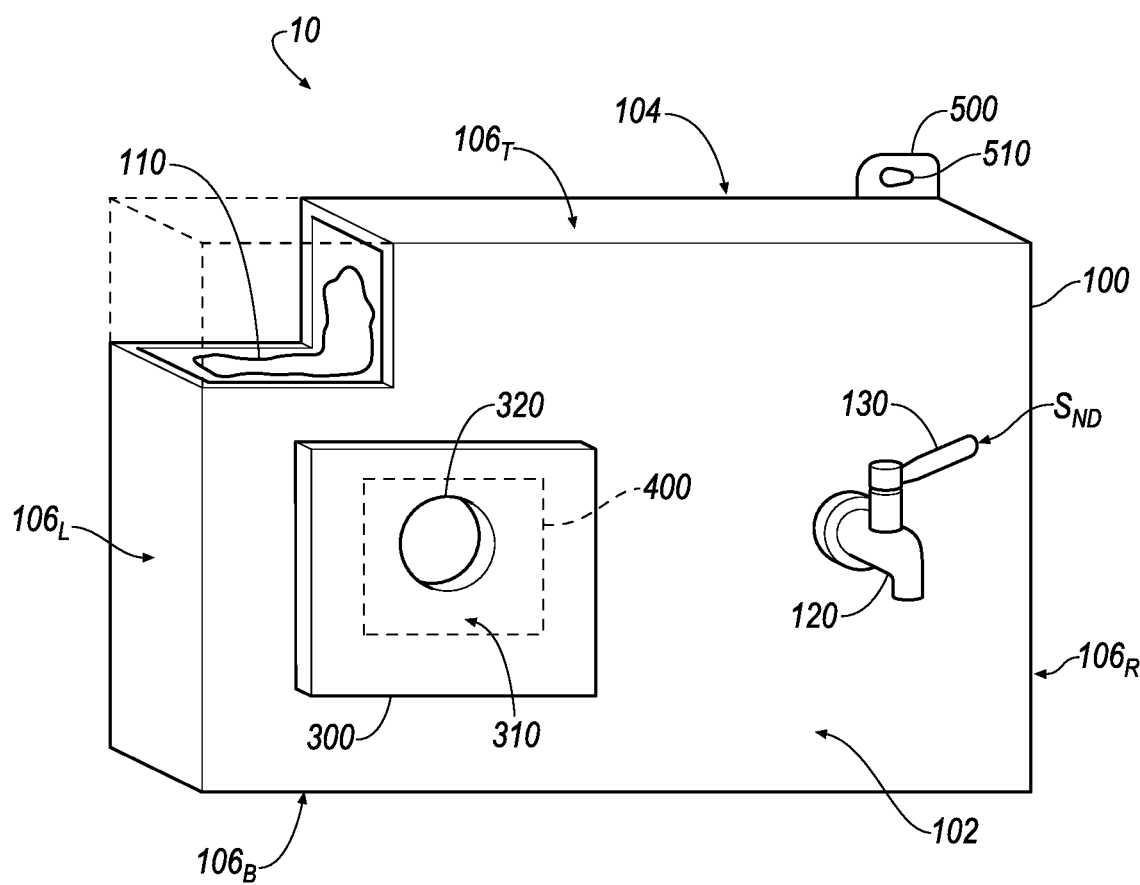
FIG. 4 is a front perspective view of an apparatus for dispensing sanitizing fluid.

FIG. 4 is an example of the apparatus 10 where the at least one applicator pad 300 is mounted on the front wall 102 of the housing 100 adjacent to the dispensing valve 120. Embodiments, such as FIG. 4, may allow the user to have varying degrees of portability. For example, the configurations of FIGS. 1A-1C may be a more permanent fixture; while, the apparatus of FIG. 4 has a mount 500 on the back wall 104 of the housing 100 to temporarily secure the apparatus 10 to objects within a healthcare environment, such as a bed frame or a clipboard. Referring to FIG. 4, the dispensing valve 120 operates similar to other dispensing valves disclosed herein except that the dispensing valve 120 is incorporated into a wall of the housing 100 that is shared with the at least one applicator pad 300.

FIG. 4 depicts component 400 (referred hereafter as "applicator pad dispensing valve 400" and previously disclosed in prior applications as "dispensing valve 60") as another dispensing valve specific to the at least one applicator pad 300. A further discussion of the applicator pad dispensing valve 400, may be found in the commonly owned U.S. Pat. App. No. 62/397,580 filed Sep. 21, 2016, with respect to dispensing valve 60 of U.S. Pat. App. No. 62/397, 580. U.S. Pat. App. No. 62/397,580 is hereby incorporated by reference in its entirety.

Figure 5A:
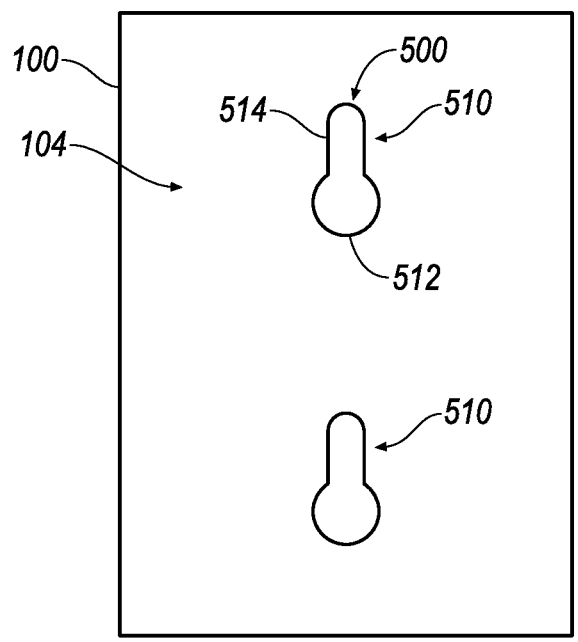
FIGS. 5A and 5B are rear views of example mounts for an apparatus for dispensing sanitizing fluid.
Figure 5B:
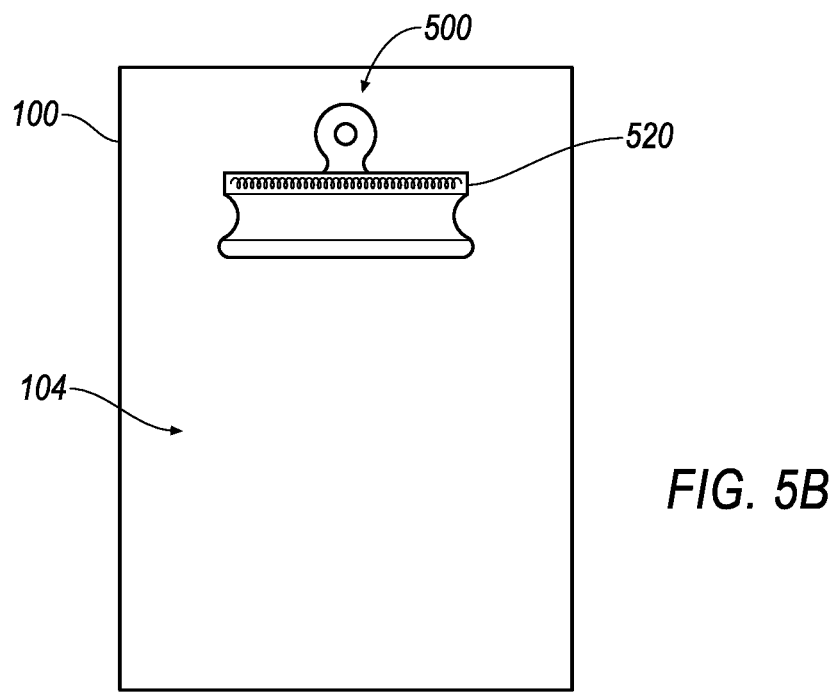

Referring now to FIGS. 5A and 5B, the apparatus 10 may further comprise a mount 500 for mounting the apparatus 10 on a variety of supporting structures, such as a wall or piece of furniture. In one embodiment, the mount 500 is configured for wall-mounting of the apparatus 10 and disposed on the back wall 104 of the housing 100. One particular construction employs one or more slots 510 in the back wall 104 of the housing 100. The slots 510 may be configured for mounting the apparatus 10 on one or more nail or screw heads, such as for mounting the apparatus 10 on a wall. As such, the slots 510 may be key-hole slots and have a rounded lower portion 512 for accepting the nail or screw head through the slot 510 and a narrow upper portion 514 for sliding over the shaft of the nail or screw positioned therein.

In another embodiment, shown in FIG. 5B, the mount 500 may be a spring-loaded clip 520 attached to the back wall 104 of the housing 100. The clip 520 permits the apparatus 10 to be removably mounted on an object of furniture, such as a bed frame, at the point of care. The clip 520 may also be used to mount the apparatus 10 on a medical practitioner's clipboard or allow it to double as a clipboard.

The sanitizing fluid S contained in the reservoir 110 of the apparatus 10 may be any fluid known in the art to be suitable for disinfecting surfaces. For example, the sanitizing fluid S may be an alcohol-based disinfectant, a benzalkonium chloride-based disinfectant, or any other fluid suitable for disinfecting surfaces. A benzalkonium chloride-based disinfectant, known as the surfactant, allantoin, and benzalkonium chloride ("SAB") disinfectant has been described previously. See, e.g., David L. Dyer et al., Testing a New Alcohol-Free Hand Sanitizer to Combat Infection, 68 AORN J. 239 (1998), the entire contents of which are incorporated herein by reference. In one embodiment, the sanitizing fluid S is an alcohol-based disinfectant, such as an ethanol—or isopropanol-based disinfectant, or any other suitable alcohol-based disinfectant.

A number of implementations have been described. Nevertheless, it will be understood that various modifications may be made without departing from the spirit and scope of the disclosure. Accordingly, other implementations are within the scope of the following claims.

What is claimed is:

1. An apparatus comprising:
    a housing having a reservoir for retaining sanitizing fluid;
    a holder disposed beneath the housing;
    an applicator pad received by the holder and adapted to receive sanitizing fluid from the reservoir, the applicator pad comprising a wetting area and a raised portion, the wetting area configured to receive sanitizing fluid, the a raised portion disposed within the wetting area and configured to extend at least partially into an interior region of a bell of a stethoscope head when the bell is placed over the raised portion, and
    a dispensing valve facing the applicator pad and configured to dispense the sanitizing fluid, the applicator pad offset from the dispensing valve by a dispensing distance, and
    wherein, at the dispensing distance, the sanitizing fluid from the dispensing valve disperses over a dispersion area dimensionally proportional to the wetting area.

2. The apparatus of claim 1, wherein the dispensing valve has a dispensing state and a non-dispensing state, the dispensing valve configured to dispense the sanitizing fluid from the dispensing valve on the applicator pad only when the dispensing valve is in the dispensing state.

3. The apparatus of claim 2, further comprising a lever, the lever configured to activate the dispensing valve to transition from the non-dispensing state to the dispensing state.

4. The apparatus of claim 1, wherein the applicator pad is an absorbent material to absorb the sanitizing fluid.

5. The apparatus of claim 4, wherein the absorbent material of the applicator pad is porous and comprises at least one of a cloth material, a cellulose sponge material, or a synthetic polymer sponge material.

6. The apparatus of claim 1, wherein the applicator pad further comprises a substantially planar portion configured to receive a diaphragm of the stethoscope head when a surface of the diaphragm is placed in contact with the substantially planar portion of the applicator pad.

7. The apparatus of claim 1, wherein the raised portion includes a substantially hemi-spherical shape having a radius between about 0.50 cm and 1.00 cm.

8. The apparatus of claim 3, further comprising a passage from the reservoir to the applicator pad.

9. The apparatus of claim 8, wherein activation of the lever dispenses sanitizing fluid through both the dispensing valve and the passage to the applicator pad.

10. The apparatus of claim 8, wherein the passage is configured for fluid communication with the applicator pad independently from the dispensing valve.

11. The apparatus of claim 10, further comprising a second lever configured to dispense sanitizing fluid through the passage to the applicator pad when the second lever is activated.

12. The apparatus of claim 1, further comprising a mount disposed on the housing, the mount configured for wall-mounting and having one or more slots on the housing, the one or more slots configured to receive a fastener for mounting the housing.

13. The apparatus of claim 1, wherein the raised portion includes a dome-shaped geometry.

14. The apparatus of claim 13, wherein the dome-shaped geometry is hemi-spherical.

15. The apparatus of claim 1, wherein the raised portion includes at least one of a conical and a frustoconical geometry.

16. An apparatus comprising:
    a housing having a reservoir for retaining sanitizing fluid;
    a holder disposed beneath the housing, the holder comprising a dome-shaped portion having a substantially hemi-spherical shape configured to extend into an interior region of a bell of a stethoscope head when the bell is placed over the dome-shaped portion;
    an applicator pad received by the holder and adapted to be in selective fluid communication with the reservoir; and
    a dispensing valve coupled to the housing and facing the applicator pad, the dispensing valve configured to dispense the sanitizing fluid.

17. The apparatus of claim 16, wherein the applicator pad has a top surface and an opposite bottom surface, the top surface facing the dispensing valve, the bottom surface having a concave region for receiving the dome-shaped portion of the holder.

18. The apparatus of claim 17, wherein the top surface of the applicator pad is substantially planar.

19. The apparatus of claim 18, further comprising a lever, the lever configured to activate the dispensing valve to transition from a non-dispensing state to a dispensing state.

20. The apparatus of claim 16, wherein the applicator pad and the dispensing valve are offset by a dispensing distance, the dispensing distance defined by a dispersion area of the sanitizing fluid from the dispensing valve, the dispersion area having a dimensional proportionality to a wetting area of the applicator pad.

21. An apparatus comprising:
    a housing having a front wall and a back wall, the housing encasing a reservoir for retaining sanitizing fluid;
    an applicator pad mounted on the front wall of the housing and adapted to be in selective fluid communication with the reservoir, the applicator pad comprising a dome-shaped portion having a substantially hemi-spherical shape configured to extend into an interior region of a bell of a stethoscope head when the bell is placed over the dome-shaped portion; and
    a dispensing valve coupled to the housing adjacent to the applicator pad on the front wall of the housing, the dispensing valve having a non-dispensing state and a dispensing state, the dispensing valve configured to dispense the sanitizing fluid when in the dispensing state; and
    a mount disposed on the back wall of the housing, the mount configured for wall-mounting and having one or more slots in the back wall of the housing, the one or more slots configured to receive a fastener for mounting the housing.

22. An apparatus comprising:
    a housing having a reservoir for retaining sanitizing fluid;
    a holder disposed beneath the housing;
    an applicator pad received by the holder and adapted to receive sanitizing fluid from the reservoir, the applicator pad comprising a wetting area and a raised portion, the wetting area configured to receive sanitizing fluid, the a raised portion disposed within the wetting area and configured to extend at least partially into an interior region of a bell of a stethoscope head when the bell is placed over the raised portion;

a dispensing valve facing the applicator pad and having a dispensing state and a non-dispensing state, the dispensing valve configured to dispense the sanitizing fluid from the dispensing valve on the applicator pad only when the dispensing valve is in the dispensing state;

a passage from the reservoir to the applicator pad, the passage configured to fluidly communicate with the applicator pad independently from the dispensing valve; and more than one lever configured to dispense sanitizing fluid through the passage and the dispensing valve, the more than one lever comprising a first lever and a second lever, the first lever configured to activate the dispensing valve to transition the dispensing valve from the non-dispensing state to the dispensing state, the second lever configured to dispense sanitizing fluid through the passage.

* * * * *

UNITED STATES PATENT AND TRADEMARK OFFICE
CERTIFICATE OF CORRECTION

| | |
|---|---|
| PATENT NO. | : 10,806,814 B2 |
| APPLICATION NO. | : 15/711804 |
| DATED | : October 20, 2020 |
| INVENTOR(S) | : Mark D. Kolins et al. |

Page 1 of 1

It is certified that error appears in the above-identified patent and that said Letters Patent is hereby corrected as shown below:

In the Claims

At Column 11, Claim number 1, Line number 17, delete "the a raised portion" and insert --the raised portion--.

At Column 12, Claim number 22, Line number 64, deleted "the a raised portion" and insert --the raised portion--.

Signed and Sealed this
Nineteenth Day of January, 2021

Andrei Iancu
*Director of the United States Patent and Trademark Office*